United States Patent [19]

Gulyás et al.

[11] Patent Number: 4,758,552

[45] Date of Patent: Jul. 19, 1988

[54] GONADOLIBERIN DERIVATIVES CONTAINING AN AROMATIC AMINOCARBOXYLIC ACID IN THE 6-POSITION, PHARMACEUTICAL AND VETERINARY COMPOSITIONS CONTAINING THEM AND PROCESS FOR PREPARING SAME

[75] Inventors: Tamás Gulyás, Szekszárd; István Teplán, Budapest; Anikó Horváth, Budapest; György Kéri, Budapest; Bökönyi Istváné, Budapest; Sándor Vigh, Pécs, all of Hungary

[73] Assignee: Innofinance Altalanos Innovacios Penzintezet, Budapest, Hungary

[21] Appl. No.: 177

[22] Filed: Jan. 2, 1987

[30] Foreign Application Priority Data

Jan. 3, 1986 [HU] Hungary .................................. 16/86

[51] Int. Cl.$^4$ ........................ A61K 37/43; C07K 7/20
[52] U.S. Cl. ...................................... 514/15; 514/800; 530/313
[58] Field of Search ................... 530/313; 514/15, 800

[56] References Cited

U.S. PATENT DOCUMENTS 4,292,313 9/1981 Vale, Jr. et al. ..................... 530/313
4,647,553 3/1987 Gulyas et al. ....................... 530/313
4,677,193 6/1987 Rivier et al. ........................ 530/313

Primary Examiner—Delbert R. Phillips
Attorney, Agent, or Firm—Keil & Weinkauf

[57] ABSTRACT

The invention relates to novel gonadoliberin nonapeptide ethylamide or decapeptide amide derivatives of the general formula (I), $$\text{Glp-His-Trp-Ser-Tyr-}X_1\text{-}X_2\text{-}X_3\text{-Pro-}X_4 \qquad (I)$$

wherein $X_1$ stands for a 2-aminobenzoic or 3-aminobenzoic acid group;

$X_2$ stands for a leucyl, tryptophyl or phenylalanyl group;

$X_3$ means an arginyl, leucyl or glutaminyl group; and $X_4$ represents a glycylamide or ethylamide group, as well as their acid addition salts and pharmaceutical presparations containing these compounds. Further on, the invention relates to a process for preparing these compounds and preparations.

The gonadoliberin derivatives of the invention can more effectively be used for reproduction biological purposes as compared to the derivatives known so far.

4 Claims, No Drawings

GONADOLIBERIN DERIVATIVES CONTAINING AN AROMATIC AMINOCARBOXYLIC ACID IN THE 6-POSITION, PHARMACEUTICAL AND VETERINARY COMPOSITIONS CONTAINING THEM AND PROCESS FOR PREPARING SAME

The invention relates to novel gonadoliberin nonapeptide ethylamide or decapeptide amide derivatives of the general formula (I), Glp-His-Trp-Ser-Tyr-$X_1$-$X_2$-$X_3$-Pro-$X_4$ (I)

wherein $X_1$ stands for a 2-aminobenzoic or 3-aminobenzoic acid group;

$X_2$ stands for a leucyl, tryptophyl or phenylalanyl group;

$X_3$ means an arginyl, leucyl or glutaminyl group; and $X_4$ represents a glycylamide or ethylamide group, as well as their acid addition salts and pharmaceutical preparations containing these compounds.

According to an other aspect of the invention there is provided a process for the preparation of the new compounds of the general formula (I) and their salts.

The abbreviations used in the formulae are in agreement with the nomenclature accepted in the peptide chemistry [see, e.g.: J. Biol. Chem. 241, 527 (1966)]. Thus, the meanings of the abbreviations used in this description are as follows.

| X | | -X- |
|---|---|---|
| Glp: | pyroglutamic acid | (pyroglutamyl) |
| His: | histidine | (histidyl) |
| Trp: | tryptophan | (tryptophyl) |
| Ser: | serine | (seryl) |
| Tyr: | tyrosine | (tyrosyl) |
| Gly: | glycine | (glycyl) |
| Phe: | phenylalanine | (phenylalanyl) |
| Leu: | leucine | (leucyl) |
| Pro: | proline | (prolyl) |
| Glu: | glutamic acid | (glutamyl) |
| Gln: | glutamine | (glutaminyl) |
| Arg: | arginine | (arginyl) |
| Mab: | 3-aminobenzoic acid | |
| Aa: | anthranilic acid | |
| Boc: | tertiary-butyloxycarbonyl | |
| Bzl: | benzyl | |
| DCC: | dicyclohexylcarbodiimide | |
| DCU: | dicyclohexylurea | |
| DIC: | diisopropylcarbodiimide | |
| DMF: | dimethylformamide | |
| DNP: | dinitrophenyl | |
| EA: | ethylamide | |
| Et: | ethyl | |
| HPLC: | high performance liquid chromatography | |
| Me: | methyl | |
| ONP: | 4-nitrophenyl | |
| OPCP: | pentachlorophenyl | |
| OPFP: | pentafluorophenyl | |
| TEA: | triethylamine | |
| TFA: | trifluoroacetic acid | |
| THF: | tetrahydrofuran | |
| TLC: | thin layer chromatography | |
| Tos: | tosyl | |
| UV: | ultraviolet | |
| Z: | benzyloxycarbonyl | |

A common property of gonadoliberin [other names known from the literature: gonadotropin releasing hormone, GnRH, luteinizing and follicle-stimulating hormone releasing hormone (LH/FSH-RH); chemically /Glp-His-Trp-Ser-Tyr-Gly-Leu-Arg-Pro-Gly-$NH_2$] and of the known derivatives of this hormone consists in the ability to release the luteinizing the follicle-stimulating hormones (LH and FSH).

At the beginning of the 80's, it has become known that the structure of the gonadoliberin in some fish and birds is different from that of the gonadoliberin found in the mammals [J. A. King and R. P. Millar: J. Biol. Chem. 257, 10722 (1982); South-African J. of Science 78, 124 (1982); N. Sherwood et al.: Proc. Natl. Acad. Sci. 80, 2794 (1983)]. These differences affect the aminoacids in the 8-position in case of birds and those in the 7- or 8-position, respectively, in case of fish.

It is also known from the literature that gonadoliberin derivatives containing D-aminoacids with a hydrophobic aliphatic or aromatic side-chain, instead of the glycine present in the 6-position, possess an increased effect as compared to that of gonadoliberin [J. Sandow et al.: "Control of Ovulation", Ed. Butterworth, London 1978, 49-70; A. V. Schally et al.: Ann. Rev. Biochem., 47, 89 (1978)].

Further on, it is known that the biological activity of gonadoliberin can be enhanced to a higher level on replacing the glycinamide group in the 10-position by amide groups containing an aliphatic chain [M. Fujino et al.; J. Med. Chem. 16, 1144 (1973)].

While investigating the energy content of the various possible conformations of the decapeptide, F. A. Momany [J. Amer. Chem. Soc. 98, 2990 (1976); and ibidem 98, 2996 (1976)] proved that the lowest energy content is represented by a spatial arrangement, wherein the molecule is bent in an "U" form (β-turn) at the glycine or D-alanine in the 6-position. R. M. Freidinger et al. [Science 210, 656 (1980)] prepared a GnRH derivative of the formula (IV),

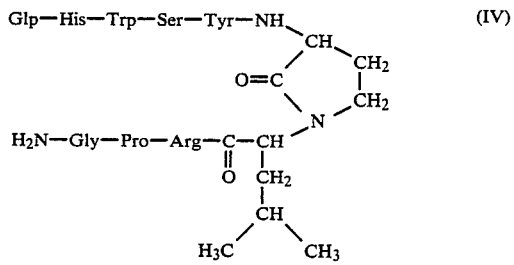

wherein this spatial structure was fixed by replacing the glycine in the 6-position with a γ-lactam. The biological activity of this compound was increased as compared to that of the native gonadoliberin.

The aim of the invention is to prepare novel gonadoliberin derivatives showing a more preferable biological efficiency in comparison to that of the known compounds, useful to propagate other species such as fish and amphibians in addition to the propagation of mammals.

An other aim of the invention is to develop a process, wherein, instead of glycine in 6-position, a novel-type aminoacid is built in, which contains the aromatic ring increasing the biological activity in addition to the fixation of the most preferable spatial arrangement and, simultaneously, to avoid the risk of racemization.

The invention is based on the recognition that the above aim can be achieved by building in a 2-aminobenzoic acid group (anthranilic acid) of the formula (V)

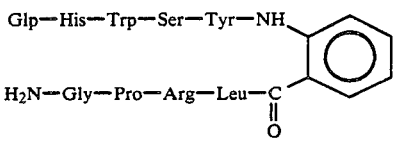

or a 3-aminobenzoic acid group of the formula (VI)

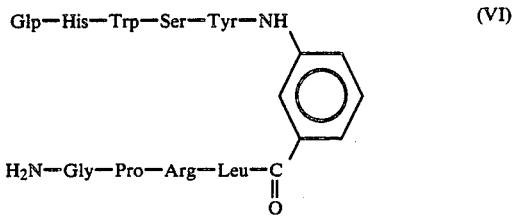

instead of the glycine group in 6-position of gonadoliberin.

A further basis of the invention is the recognition that the efficiency of such gonadoliberin derivatives can further be increased by replacing the glycine amide group in 10-position by an alkylamide group containing 1 to 4 carbon atoms.

Finally, the invention is based on the recognition that on replacing the aminoacids in 8-position or in 7- and 8-positions of gonadoliberin by certain aminoacids, gonadoliberin derivatives can be prepared which are useful to propagate other species in addition to mammals.

Based on these facts, there is provided a process for preparing the nonapeptide ethylamide or decapeptide amide compounds of the general formula (I), wherein $X_1$, $X_2$, $X_3$ and $X_4$ are the same as defined above, and their salts, which comprises (a) condensing the protected amino acids by using the appropriate combinations of the stepwise and fragment condensation and removing the protective groups, or (b) condensing stepwise, by using the solid phase peptide synthetic method, the protected aminoacids to a solid carrier in the appropriate order by means of the carbodiimide or active ester method, splitting the final product from the solid carrier by an acidic or alkaline cleavage and removing the protective groups simultaneously with or before or after the cleavage from the resin.

A particularly preferred embodiment of the combinations according to process (a) comprises condensing a pentapeptide azide of the formula (II)

Glp-His-Trp-Ser-Tyr-N₃   (II)

with a tetrapeptide or pentapeptide of the general formula (III),

X₁-X₂-X₃-Pro-X₄,   (III)

wherein $X_1$, $X_2$, $X_3$ and $X_4$ are the same as defined above.

In process (b), it is suitable to use a benzhydrylamine resin or a chloromethylated polystyrene resin as a solid carrier (solid phase).

It is convenient to remove the final product containing the protective groups by cleaving with hydrogen fluoride and/or by using ethylammonolysis.

The thus-obtained nona- or decapeptide amide can be transformed, if desired, to an acid addition salt by reacting it with a pharmaceutically acceptable acid or, if desired, the free base can be liberated from the acid addition salt by reacting it with a base.

The invention also relates to compositions useful for therapeutical and/or reproduction biological purposes which contain the compounds of the general formula (I) or an acid addition salt thereof as active ingredient.

Further on the invention also refers to a process for the preparation of these compositions which comprises mixing a compound of the general formula (I) or an acid addition salt thereof with the commonly used vehicles and/or carrier materials to obtain a composition useful for therapeutic and/or reproduction biological purposes.

In case of cattles, the gonadoliberin derivatives of the general formula (I) are effective in a dose interval of 5 to 200 μg when administered intramuscularly, subcutaneously or intravenously, whereas in case of fish they are active in a dose interval of 0.1 to 100 μg when injected intramuscularly or subcutaneously.

The important advantages of novel gonadoliberin derivatives of formula (I) and of the process of the invention are as follows:

(a) The novel gonadoliberin derivatives are more effective in comparison to the gonadoliberin derivatives known so far, according to reproduction biological experiments carried out on cattles and fish.

(b) The new substituents built in the 6-position do not contain any centre of asymmetry, whereby no racemisation can occur and the preparation of the final product is made easier and cheaper.

(c) The costs of the preparation of 2- and 3-aminobenzoic acid are much lower than those of the D-aminoacids playing a similar role in the known GnRH derivatives.

(d) The pentapeptide component of the formula (II) used as a starting substance in the process (a) is the common intermediate of each final product.

The invention is illustrated in detail by the aid of the following non-limiting Examples, where the thin layer chromatography (TLC) R_f values were determined on Kieselgel (DC Alufolien, Merck) sheets by using the following solvent systems referred to with number above the signs "R_f":

| | | |
|---|---|---|
| 1. | Ethyl acetate/pyridine/acetic acid/water | 30:20:6:11 |
| 2. | Ethyl acetate/pyridine/acetic acid/water | 60:20:6:11 |
| 3. | Ethyl acetate/pyridine/acetic acid/water | 120:20:6:11 |
| 4. | Ethyl acetate/pyridine/acetic acid/water | 240:20:6:11 |
| 5. | n-Butanol/acetic acid/water/ethyl acetate | 1:1:1:1 |
| 6. | n-Butanol/acetic acid/water | 4:1:1 |
| 7. | Isopropanol/1 molar acetic acid | 2:1 |
| 8. | Ethyl acetate/pyridine/acetic acid/water | 5:5:1:3 |
| 9. | Acetone/toluene | 1:1 |
| 10. | Chloroform/acetic acid | 24:2 |
| 11. | Butanone/pyridine/water | 65:15:20 |
| 12. | Chloroform/metanol/acetic acid | 85:10:5 |
| 13. | n-Butanol/acetic acid/ammonia (1 vol. of concentrated ammonium hydroxide + 4 vols. of water)/water | 6:1:1:2 |

EXAMPLE 1

Preparation of [Aa⁶, Gln⁸, desGly¹⁰]-gonadoliberin ethylamide

Step (a)

Preparation of Boc-His(DNP)-Trp-OMe (molecular weight: 622.62)

21.12 g (50 mmoles) of Boc-His(DNP)-OH are dissolved in 100 ml of DMF and cooled to 0° C., then 10.32 g (50 mmoles) of DCC and 7.66 g (50 mmoles) of N-hydroxybenzotriazole are added under stirring. After stirring the mixture at 0° C. for 10 minutes, the precipitated DCU is filtered out.

The solution of 12.74 g (50 mmoles) of H-Trp-OMe.HCl in 70 ml of DMF is cooled to 0° C., 6.94 ml (50 mmoles) of TEA are added and after stirring for 5 minutes the precipitated triethylamine hydrochloride is filtered out.

The above two solutions are combined and stirred at 0° C. overnight. The DCU precipitate is filtered and the solution is evaporated to dryness. The oily residue is dissolved in 500 ml of ethyl acetate and extracted 3 times with 100 ml of ice-cold 1 molar potassium hydrogen sulfate solution each, then 5 times with 100 ml of saturated sodium hydrogen carbonate solution each and finally twice with 100 ml of 10% sodium chloride solution each. The organic phase is dried over anhydrous magnesium sulfate, filtered and evaporated to dryness. The oily residue is thoroughly triturated with petroleum ether and the obtained powder is filtered and dried. The thus-obtained crystalline product is recrystallized from ethyl acetate with petroleum ether to give the aimed product in a yield of 27.70 g (89%), m.p.: 119°–122° C.

$[\alpha]_D^{22} = +14.1°$ (c=1, DMF).
$R_f^4 = 0.62$; $R_f^5 = 0.41$.

Step (b)

Preparation of H-His(DNP)-Trp-OMe.2HCl [molecular weight: 522.49 (free base); 595.41 (dihydrochloride)]

100 ml of 4N methanolic hydrogen chloride solution are added to the solution containing 24.9 g (40 mmoles) of Boc-His(DNP)-Trp-OMe dipeptide in 100 ml of methanol. The mixture is set aside for 30 minutes at room temperature whilst the dipeptide ester hydrochloride crystallizes. The precipitate is filtered, washed with ether and dried to give 21.91 g (92%) of the aimed compound, m.p.: 198°–202° C.

$[\alpha]_D^{22} = 0.49°$ (c=1, DMF).
$R_f^3 = 0.46$; $R_f^4 = 0.18$.

Step (c)

Preparation of Glp-His-(DNP)-Trp-OMe (molecular weight: 633.60)

The mixture containing 4.85 g (36.8 mmoles) of L-pyroglutamic acid, 7.58 g of DCC and 5.63 g of N-hydroxybenzotriazole in 100 ml of DMF is stirred at 5° to 10° C. for 10 minutes, then the DCU precipitate is filtered.

9.72 ml (70 mmoles) of TEA are added to the solution of 20.84 g (35 mmoles) of H-His(DNP)-Trp-OMe.2HCl in 100 ml of DMF. After stirring for 5 minutes, the precipitated triethylamine hydrochloride is filtered. Both solutions are combined and stirred at room temperature overnight. Next day 90 ml of acetone are added and the insoluble precipitate is filtered. The oily residue obtained after evaporation is thoroughly triturated with ethyl acetate, filtered and dried. The dry crystalline product is washed 3 times with 25 ml of water each and dried again. The thus-obtained product is recrystallized from hot ethyl acetate to give the aimed compound in a yield of 18.42 g (83.1%), m.p.: 148°–151° C.

$[\alpha]_D^{23} = +5.2°$ (c=1, DMF).
$R_f^3 = 0.53$; $R_f^7 = 0.38$.

Step (d)

Preparation of Glp-His-Trp-OMe (molecular weight: 466.50)

To the solution containing 15.84 g (25 mmoles) of Glp-His(DNP)-Trp-OMe protected tripeptide in 100 ml of DMF and 40 ml of water, 4 ml of mercaptoethanol are added, then the pH-value of the solution is adjusted to 8 by adding TEA. The solution is left to stand at room temperature for 30 minutes, then evaporated to dryness under reduced pressure. The oily residue is thoroughly triturated with ether, filtered and dried. The thus-obtained product is dissolved in a little volume of methanol and crystallized by adding ether. The crystals are filtered and dried to give 10.92 g (93.5% yield) of the aimed compound, m.p.: 228°–232° C.

$[\alpha]_D^{22} = +4.04°$ (c=0.42, DMF).
$R_f^2 = 0.30$.

Step (e)

Preparation of Glp-His-Trp-$N_2H_3$ (molecular weight: 466.51)

20 ml of 98% hydrazine hydrate are added to a solution containing 9.33 g (20 mmoles) of Glp-His-Trp-OMe tripeptide in 250 ml of methanol. The mixture is stirred at 40° C. for 3 hours and then at room temperature overnight. Next day the precipitate is filtered, washed with cold methanol and dried to give 7.58 g (81.2% yield) of the aimed compound, m.p.: 166°–169° C.

$[\alpha]_D^{22} = -22.3°$ (c=0.5, DMF).
$R_f^1 = 0.50$; $R_f^2 = 0.14$.

Step (f)

Preparation of Glp-His-Trp-Ser-Tyr-OMe (molecular weight: 716.8)

The solution of 7.0 g (15 mmoles) of Glp-His-Trp-$N_2H_3$ [prepared as described in the preceding Step (e)] in 60 ml of DMF is cooled to 0° C. and 7.5 ml (45 mmoles) of 6N hydrochloric acid solution are added while stirring. Then, a concentrated aqueous solution of 1.035 g (15 mmoles) of sodium nitrite is slowly dropped to the mixture and stirred at 0° C. for additional 15 minutes. A solution of 4.78 g (15 mmoles) of H-Ser-Tyr-OMe.HCl in 15 ml of DMF is added, whereupon the pH value of the mixture is adjusted to neutral by adding 6.25 ml (45 mmoles) of TEA. The mixture is stirred at 0° to 4° C. overnight, then evaporated to dryness under reduced pressure. After thoroughly triturating the oily residue with ether and drying a powder is obtained in a yield of 12.1 g (100%) which shows two little contaminating spots on the TLC, however it can be converted without purification to the hydrazide which is well crystallizable. After recrystallizing a sample from methanol, the aimed compound melts at 188°–190° C.

$[\alpha]_D^{22} = -3.48°$ (c=1, DMF).
$R_f^1 = 0.58$; $R_f^2 = 0.26$.

Step (g)

Preparation of Glp-His-Trp-Ser-Tyr-$N_2H_3$ (molecular weight: 716.8)

After adding 10 ml of 98% hydrazine hydrate to a solution containing 12 g of crude, powdered Glp-His-Trp-Ser-Tyr-OMe pentapeptide ester in 200 ml of methanol, the mixture is stirred at 40° C. for 3 hours. Thereafter the mixture is stirred at room temperature overnight, then the crystalline precipitate is filtered and dried in a desiccator over concentrated sulfuric acid.

The dried crystals are dissolved in 250 ml of 0.5N hydrochloric acid solution, neutralized to a pH value of 8 by adding saturated sodium carbonate solution and left to stand at 0° C. for 2 hours. The crystalline precipitate is filtered, washed with ice-cold water and dried to give 6.12 g (56.9% yield as calculated for two steps together) of the aimed compound, m.p.: 205°–206° C.
$[\alpha]_D^{22} = 21.51°$ (c=1, DMF).
$R_f^1 = 0.39$; $R_f^2 = 0.14$.

The analysis of the hydrazine nitrogen gave 3.79% and 3.76% (the calculated value is 3.91%).

Step (h)

Preparation of H-Gln-Pro-NHEt.TFA [molecular weight: 367.3 (Boc: 370.49)]

10 g (70 mmoles) of proline ethylamide (obtained by the hydrogenation of 72 mmoles of Z-Pro-NHEt) are dissolved in 100 ml of DMF and the pH value of the solution is adjusted to 8 by adding TEA. A solution containing 32 g (87 mmoles) of Boc-Gln-ONP in 100 ml of DMF is added under stirring.

The oily residue is dissolved in a mixture containing 50 ml of 30% TFA in dichloromethane and left to stand at room temperature for 20 minutes. Subsequently, the solution is evaporated under reduced pressure and the oily residue is thoroughly triturated with ether. The thus-obtained solid product is washed with ether and dried under reduced pressure to give 15.9 g (62% yield) of the aimed product, the melting point of which cannot be measured because of its strong hygroscopic character.
$[\alpha]_D^{20} = -44.4°$ (c=1, methanol).
$R_f^1 = 0.32$; $R_f^7 = 0.37$; $R_f^{13} = 0.21$.

Step (i)

Preparation of Z-Leu-Gln-Pro-NHEt (molecular weight: 518.57)

7 g (26 mmoles) of H-Gln-Pro-NHEt.TFA are dissolved in 50 ml of DMF, cooled to 0° C., then the pH value of the solution is adjusted to 8 by adding TEA. A solution containing 14 g (27.3 mmoles) of Z-Leu-pentachlorophenyl ester in 40 ml of DMF is added and stirred at 4° C. overnight. Next day the mixture is evaporated under reduced pressure and the residue is dissolved in 70 ml of ethyl acetate. The organic solution is extracted 3 times with 15 ml of cold 0.01N sodium hydroxide solution each, then 3 times with 15 ml of water wach. The sodium hydroxide and the aqueous extract are combined and washed twice with 10 ml of ethyl acetate each. After combining the ethyl acetate solution is dried over anhydrous sodium sulfate and evaporated under reduced pressure. The residue is thoroughly triturated with ether, the thus-obtained solid product is filtered, washed with ether and dried under reduced pressure to give 10.4 g (77% yield) of the aimed product, m.p.: 84°–88° C.
$[\alpha]_D^{20} = -32.8°$ (c=1, methanol).
$R_f^2 = 0.90$.

Step (j)

Preparation of H-Leu-Gln-Pro-NHEt.HBr (molecular weight: 465.5)

70 ml of a 4N solution of hydrogen bromide in glacial acetic acid are added to a solution containing 7.6 g (14.6 mmoles) of Z-Leu-Gln-Pro-NHEt in 50 ml of glacial acetic acid, then the mixture is left to stand at room temperature for 90 minutes. The mixture is slowly poured into 800 ml of ice-cold ether while stirring. After 30 minutes, the stirring is stopped and the settled precipitate is filtered and dried in a desiccator over phosphorus pentoxide to give 7.9 g of the aimed product, m.p.: 147° C.
$[\alpha]_D^{20} = -72.8°$ (c=1, 2N acetic acid).
$R_f^2 = 0.30$; $R_f^{11} = 0.82$.

Step (k)

Preparation of Boc-anthranilic acid (molecular weight: 237.27)

The pH value of a solution containing 4 g (30 mmoles) of anthranilic acid in 20 ml of DMF is adjusted to 8 by adding TEA. After adding 9 g of tertiary-butyloxy carbonate, the reaction mixture is stirred at room temperature overnight. The solvent is evaporated and the thick oily residue is dissolved in 50 ml of ethyl acetate. The organic phase is washed 3 times with 20 ml of ice-cold 0.01N sulfuric acid each, then 3 times with 20 ml of water each. The ethyl acetate solution is dried over anhydrous sodium sulfate and evaporated under reduced pressure. The thick oily residue becomes crystalline when kept in a refrigerator. The aimed product is obtained in a yield of 5.7 g (80%), m.p.: 91°–93° C.
$R_f^9 = 0.87$; $R_f^{10} = 0.79$.

Step (l)

Preparation of Boc-Aa-Leu-Gln-Pro-NHEt (molecular weight: 603.85)

The solution containing 2.3 g (5 mmoles) of H-Leu-Gln-Pro-NHEt hydrobromide in 10 ml of DMF is cooled to 0° C., then the pH value of the solution is adjusted to 8 by adding TEA. After the addition of 750 mg (5.5 mmoles) of N-hydroxybenzotriazole and 1.1 g (5.5 mmoles) of DCC, a solution containing 1.3 g (5.5 mmoles) of Boc-anthranilic acid in 5 ml of DMF is slowly dropped in, then the reaction mixture is stirred at room temperature for 48 hours. The precipitated DCU is filtered, then the solution is evaporated under reduced pressure. The residue is dissolved in 50 ml of ethyl acetate and washed 3 times with 20 ml of 10% citric acid each, then 3 times with 20 ml of water each, 3 times with 20 ml of saturated sodium hydrogen carbonate solution each and finally with 20 ml of saturated sodium chloride solution. The ethyl acetate layer is dried over anhydrous sodium sulfate and evaporated under reduced pressure. The oily residue is thoroughly triturated with ether and the pale yellow, powder-like precipitate is filtered and washed with ether to give 2.4 g (80% yield) of the aimed product, m.p.: 119°–121° C.
$R_f^9 = 0.91$.

The aminoacid analysis gave the following values: Gln 0.97; Pro 1.03; Leu 1.00; Aa 0.92.

Step (m)

Preparation of H-Aa-Leu-Gln-Pro-NHEt.TFA (molecular weight: 599.63)

603 mg (1 mmole) of Boc-Aa-Leu-Gln-Pro-NHEt are dissolved in 10 ml of a solution containing 30% of trifluoroacetic acid (TFA) in dichloromethane and the solution is stirred at room temperature for 20 minutes. Then the TFA is rapidly removed under reduced pressure, the residue is powdered by adding ether and dried to give the aimed product in a yield of 5.15 mg (86%).
$R_f^5 = 0.52$.

Step (n)

Preparation of Glp-His-Trp-Ser-Tyr-Aa-Leu-Gln-Pro-NHEt (molecular weight: 1188.48)

A solution of 358 mg (0.5 mmole) of Glp-His-Trp-Ser-Tyr-N$_2$H$_3$ pentapeptide [prepared as described in the Step g) of this Example] in 10 ml of DMF is cooled to 0° C. and 0.34 ml of 6N hydrochloric acid and then a concentrated aqueous solution of 37.7 mg of sodium nitrite are dropped to this solution under stirring. After 5 minutes, 230 mg (0.5 mmole) of H-Aa-Leu-Gln-Pro-NHEt.TFA tetrapeptide dissolved in the mixture of 1 ml of DMF and 0.34 ml of TEA at 0° C. are added. If necessary, the reaction mixture is neutralized by adding TEA and stirred at 0° C. for 2 hours, then left to warm to room temperature. The DMF is removed under reduced pressure and the residue is separated by chromatography on a Sephadex G-25 column (2×95 cm) as dissolved in a 0.2N acetic acid solution. The separation is followed by UV absorption (measured at 280 nm) and TLC. The appropriate fractions are collected and lyophilized to obtain the aimed product in a yield of 315 mg (52%).

$R_f^5 = 0.58$; $R_f^7 = 0.83$; $R_f^8 = 0.72$

The aminoacid analysis gave the following values: Ser 0.91; Gln 2.03; Pro 0.95; Leu 1.00; Tyr 1.10; His 1.02; Trp 0.81; Aa 0.95.

EXAMPLE 2

Preparation of [Aa$^6$, desGly$^{10}$]-gonadoliberin ethylamide

Step (a)

Preparation of Z-Arg(NO$_2$)-Pro-NHEt (molecular weight: 465.47)

7.33 g (29.7 mmoles) of Z-Arg(NO$_2$)-OH and 1.034 g of N-hydroxy-benzotriazole are added to a solution containing 3.24 g (22.8 mmoles) of proline ethylamide in 70 ml of THF. The reaction mixture is cooled in an iced water bath and 5.34 g (25.8 mmoles) of DCC dissolved in 50 ml of THF are portionwise added under stirring. The mixture is stirred under cooling with ice for 5 hours, at room temperature for additional 20 hours, then filtered and washed with THF. The filtrate is evaporated under reduced pressure, the residue is dissolved in chloroform and successively washed 3 times with 35 ml of an 1:5 mixture of ammonium hydroxide with water each, twice with 20 ml of water each, 3 times with 35 ml of 1N hydrochloric acid each and finally twice with 20 ml of water each. The chloroformic solution is dried over anhydrous sodium sulfate, filtered, washed with chloroform, then the filtrate is evaporated. The residue is dissolved in a mixture of 35 ml of THF and 50 ml of ethyl acetate, filtered and washed with 30 ml of an 1:2 mixture of THF with ethyl acetate. After evaporating the solution, 100 ml of ethyl ether are added to the solid foamy residue. The thus-obtained product is filtered, washed with ether and dried under reduced pressure to afford 9.69 g (98% yield) of the aimed compound, m.p.: 125° C.

$[\alpha]_D^{20} = -42.5°$ (c=1, methanol).
$R_f^3 = 0.5$; $R_f^{12} = 0.72$.

Step (b)

Preparation of Z-Leu-Arg(NO$_2$)-Pro-NHEt (molecular weight: 578.65)

To a solution containing 5.6 g (11.73 mmoles) of Z-Arg(NO$_2$)-Pro-NHEt protected dipeptide ethylamide in 30 ml of glacial acetic acid, 55 ml of a 4N solution of hydrogen bromide in glacial acetic acid are added. The reaction mixture is left to stand at room temperature for 90 minutes, then 250 ml of abs. ether are added and the mixture is set aside for one hour. The supernatant is decanted from the precipitate and 100 ml of ether are added to the residue. After standing for 15 minutes, the mixture is filtered and thoroughly washed with ether. The solid hygroscopic substance is dried over phosphorus pentoxide and sodium hydroxide under reduced pressure. Thus, a slightly hygroscopic product is obtained in a yield of 6.44 g.

6.04 g (11.0 mmoles) of the above dipeptide ethylamide hydrobromide are suspended in 150 ml of chloroform and 5.5 ml of TEA are added. The suspension slowly becomes dissolved; an additional amount (2.5 ml) of TEA is added for achieving a complete dissolution. Then, a solution containing 6.4 g of Z-Leu-OPCP in 65 ml of chloroform is dropped to the reaction mixture and stirred overnight. Next day the mixture is successively extracted with 1N hydrochloric acid, then with saturated sodium chloride solution and 2N ammonium hydroxide solution and finally again with a saturated sodium chloride solution. The organic phase is dried over anhydrous sodium sulfate and evaporated under reduced pressure. The residue is thoroughly triturated with ether. The thus-obtained solid product is filtered, washed with ether and dried under reduced pressure to give 5.5 g (84.6% yield) of a crude product.

The above-obtained protected tripeptide ethylamide is dissolved in 30 ml of ethyl acetate with gentle warming, clarified by using activated carbon and washed twice with 10 ml of ethyl acetate each. To the filtrate, 75 ml of ethyl ether are portionwise added. The oily precipitate rapidly solidifies. After standing for about 2 hours, the mixture is filtered, washed with a 2:3 mixture of ethyl acetate and ether, then with ether, and dried under reduced pressure to obtain 4.7 g (74.3% yield) of the aimed compound, m.p.: 116°–118° C.

$[\alpha]_D^{20} = 57.0°$ (c=1, methanol).
$R_f^3 = 0.74$; $R_f^4 = 0.49$.

Step (c)

Preparation of H-Leu-Arg(NO$_2$)-Pro-NHEt.HBr (molecular weight: 537.4)

A solution containing 1.18 g (2 mmoles) of Z-Leu-Arg(NO$_2$)-Pro-NHEt tripeptide in 10 ml of a solution of hydrogen bromide in glacial acetic acid is stirred at room temperature for one hour. After adding 100 ml of anhydrous ether, the powder-like precipitate is filtered and the thus-obtained pale yellow powder is dried in a desiccator. Thus, the aimed compound is obtained as a pale yellow hygroscopic product in a yield of 1.30 g.
$R_f^2 = 0.14$.

Step (d)

Preparation of Boc-Aa-OPFP (molecular weight: 403.32)

The solution of 2.4 g (10 mmoles) of Boc-anthranilic acid in 20 ml of THF is cooled to 0° C., then 2.2 g (11 mmoles) of DCC and 2.0 g of pentafluorophenol dissolved in 10 ml of THF are added while stirring. The mixture is stirred at 0° C. for 3 hours, then at room temperature overnight. The solution is filtered, the precipitate is dissolved in 30 ml of ethyl acetate and successively washed 3 times with 10 ml of ice-cold 10% citric acid each, 3 times with 10 ml of cold water each, 3 times with 10 ml of saturated sodium hydrogen carbonate solution each and finally 3 times with 10 ml of water each. The ethyl acetate phase is dried over anhydrous sodium sulfate, filtered and evaporated under reduced pressure. When kept at +4° C., the oily residue becomes crystalline. Thus, the aimed product is obtained in a yield of 3.06 g (76%).
$R_f^9=0.90$; $R_f^{10}=0.85$.

Step (e)

Preparation of Boc-Aa-Leu-Arg(NO$_2$)-Pro-NHEt (molecular weight: 675.75)

A solution containing 1.07 g (2 mmoles) of H-Leu-Arg(NO$_2$)-Pro-NHEt.HBr tripeptide salt in 5 ml of DMF is cooled to 0° C. and then 0.28 ml (2 mmoles) of TEA and 806 mg (2 mmoles) of Boc-Aa-OPFP dissolved in 5 ml of DMF are added. The pH value of the solution is adjusted to 8 by adding TEA, the solution is left to warm and then stirred at 20° C. for 48 hours while maintaining the pH value at about 8 by adding TEA. DMF is removed under reduced pressure, the residue is dissolved in 50 ml of ethyl acetate and successively washed 3 times with 20 ml of 10% citric acid each, 3 times with 20 ml of water each, 3 times with 20 ml of saturated sodium hydrogen carbonate solution each and finally with 20 ml of a saturated sodium chloride solution. The ethyl acetate solution is dried over anhydrous sodium sulfate, filtered and evaporated under reduced pressure. The oily residue is thoroughly triturated with ether and the thus-obtained solid product is filtered to give 1.05 g (77.8% yield) of the aimed compound.
$R_f^3=0.90$; $R_f^9=0.91$; $R_f^{10}=0.96$.

Step (f)

Preparation of Boc-Aa-Leu-Arg-Pro-NHEt (molecular weight: 630.74)

A solution containing 1.0 g (1.5 mmoles) of Boc-Aa-Leu-Arg(NO$_2$)-Pro-NHEt tetrapeptide in 50 ml of 50% acetic acid is hydrogenated in the presence of 400 mg of 10% palladium-on-charcoal catalyst for 4 hours. Then the catalyst is filtered out, the solution is evaporated and the residue is thoroughly triturated with ether to obtain 779 mg (82.5% yield) of the aimed compound.
$R_f^2=0.45$.

Step (g)

Preparation of H-Aa-Leu-Arg-Pro-NHEt.(TFA)$_2$ (molecular weight: 724.67)

630 mg (1 mmoles) of Boc-Aa-Leu-Arg-Pro-NHEt tetrapeptide are dissolved in 5 ml of TFA and stirred at room temperature for 20 minutes. TFA is rapidly removed under reduced pressure and the residue is powdered with ether, then filtered and dried to give 648.5 mg (89.5% yield) of the aimed compound.
$R_f^2=0.34$; $R_f^8=0.76$.

Step (h)

Preparation of Glp-His-Trp-Ser-Tyr-Aa-Leu-Arg-Pro-NHEt.CH$_3$CO$_2$H (molecular weight: 1276.54)

The solution of 358 mg (0.5 mmole) of Glp-His-Trp-Ser-Tyr-N$_2$H$_3$ pentapeptide [prepared as described in Step (g) of Example 1] in 10 ml of DMF is cooled to −10° C. and first 0.34 ml of 6N hydrochloric acid and then a concentrated aqueous solution of 37.7 mg of sodium nitrite are dropwise added under stirring. After 5 minutes, a solution containing 362.3 mg (0.5 mmole) of H-Aa-Leu-Arg-Pro-NHEt.(TFA)$_2$ tetrapeptide in 1 ml of DMf and 0.34 ml of TEA prepared at −10° C. are added. The mixture is stirred at −5° C. one hour, at 0° C. for one additional hour and then left to warm to room temperature. DMF is removed under reduced pressure and the residue dissolved in 0.2N acetic acid is purified by chromatography on a Sephadex G-25 column (2×95 cm). The appropriate fractions are collected and lyophilized to give 365.7 mg (57.3% yield) of the aimed compound.
$R_f^5=0.65$; $R_f^6=0.49$; $R_f^8=0.69$.

The aminoacid analysis gave the following values: Ser 0.87; Glu 0.99; Pro 1.02; Leu 1.00; Tyr 0.97; His 1.03; Trp 0.82; Aa 0.91; Arg 1.01.

EXAMPLE 3

Preparation of [Mab$^6$]-gonadiliberin

Step (a)

Preparation of Boc-3-amino-benzoic acid (Boc-Mab) (molecular weight: 237.25)

1.0 g (7.5 mmoles) of 3-amino-benzoic acid is dissolved in 10 ml of DMf and the pH value of the solution is adjusted to 8 by adding TEA. Then 2.5 g of tertiary-butyloxy carbonate are added and the mixture is stirred for one day. The reaction mixture is worked up in the same way as described in Step (k) of Example 1 to obtain 1,4 g (80.9% yield) of the aimed compound, m.p.: 92° C.
$R_f^{10}=0.88$; $R_f^{10}=0.84$.

Step (b)

Preparation of Boc-Mab-Leu-Arg(NO$_2$)-Pro-Gly-NH$_2$ (molecular weight: 704.78)

A solution containing 1.5 g (2.5 mmoles) of H-Leu-Arg(NO$_2$)-Pro-Gly-NH$_2$.TFA salt [M. Yanaihara et al.: J. Med. Chem. 16, 373 (1973)] in 10 ml of DMF is cooled to 0° C. and the pH value of the solution is adjusted to 8 by adding TEA. Then 383 mg (2.5 mmoles) of N-hydroxy-benzotriazole and 515 mg (2.5 mmoles) of DCC are added to the solution, whereupon 593 mg (2.5 mmoles) of Boc-Mab dissolved in 3 ml of DMF are dropwise and slowly added. The reaction mixture is stirred at room temperature for 48 hours, then the precipitated DCU is filtered and the solution is evaporated under reduced pressure. The oily residue is dissolved in 30 ml of ethyl acetate and successively washed 3 times with 10 ml of 10% citric acid each, 3 times with 10 ml of water each, 3 times with 10 ml of saturated sodium hydrogen carbonate solution each and finally with 10 ml of saturated sodium chloride solution. The ethyl acetate phase is dried over anhydrous sodium sulfate and evaporated under reduced pressure. After thoroughly triturating the oily residue with ether, the white crystalline precipitate is filtered and washed with ether to give 1.2 g (68% yield) of the aimed compound, m.p.: 132°–133° C.
$R_f^6=0.43$.

Step (c)

Preparation of Boc-Mab-Leu-Arg-Pro-Gly-NH$_2$ (molecular weight: 659.78)

The protective group is removed from 1.0 g (1.5 mmoles) of Boc-Mab-Leu-Arg(NO$_2$)-Pro-Gly-NH$_2$ pentapeptide in the same manner as described in Step (f) of Example 2 to yield 775 mg (78.3%) of the aimed product.
$R_f^2=0.52$.

Step (d)

Preparation of H-Mab-Leu-Arg-Pro-Gly-NH$_2$.(TFA)$_2$ (molecular weight: 753.72)

A solution containing 670 mg (1 mmole) of Boc-Mab-Leu-Arg-Pro-Gly-NH$_2$ pentapeptide amide in 5 ml of TFA is stirred at room temperature for 20 minutes, then TFA is removed under reduced pressure. The oily residue is triturated with ether to give a powder-like product which is filtered and dried to give 689 mg (91.5% yield) of the aimed compound.

$R_f^1 = 0.50$; $R_f^5 = 0.53$; $R_f^7 = 0.42$.

Step (e)

Preparation of Glp-His-Trp-Ser-Tyr-Mab-Leu-Arg-Pro-Gly-NH$_2$ (molecular weight: 1244.39)

A solution containing 358 mg (0.5 mmole) of Glp-His-Trp-Ser-Tyr-N$_2$H$_3$ pentapeptide [prepared as described in Step (g) of Example 1] in 10 ml of DMF is cooled to $-10°$ C. and then 0.34 ml of 6N hydrochloric acid and subsequently a concentrated aqueous solution of 37.7 mg of sodium nitrite are dropwise added. After 5 minutes, 377 mg (0.5 mmole) of H-Mab-Leu-Arg-Pro-Gly-NH$_2$(TFA)$_2$ pentapeptide dissolved in 1 ml of DMf and cooled to $-10°$ C. are added. The reaction mixture is stirred at 0° C. for 2 hours, then left to warm to room temperature. Next day the mixture is evaporated under reduced pressure. The crude decapeptide residue is purified by chromagtography on a Sephadex G-25 column (2×95 cm) by using a 15:1:4:20 mixture of butanol/propanol/acetic acid/water. The component content of the fractions is followed by using TLC and UV absorption. The fraction containing the decapeptide is lyophilized, then this operation is repeated by using diluted acetic acid. The aimed product is obtained in a yield of 323 mg (52%).

$R_f^2 = 0.31$; $R_f^7 = 0.49$; $R_f^8 = 0.62$.

The aminoacid analysis gave the following values: Ser 0.91; Glu 1.03; Pro 0.97; Gly 1.10; Leu 1.00; Tyr 0.97; His 1.05; Trp 0.87; Mab 0.90; Arg 1.11.

EXAMPLE 4

Preparation of [Aa$^6$]-gonadoliberin (molecular weight: 1244.39)

(a) Synthesis

This compound is prepared by the commonly used method of the solid phase peptide synthesis [Merrifield, R. B.: J. Am. Chem. Soc. 85, 2149 (1963)].

0.75 g (0.3 mmole) of a benzhydrylamine.HCl resin (0.4 mmole/g, Pierce) is swollen in dichloromethane for 2 hours. Then, in the course of the acylation with the aminoacids, the following cycle is repeated:

| Step | Reagent and operation | Time of stirring (min.) |
|---|---|---|
| 1 | CH$_2$Cl$_2$, 3 washings | 1 |
| 2 | Mixture containing 33% of TFA and 67% of CH$_2$Cl$_2$ | 1 |
| 3 | Mixture containing 33% of TFA and 67% of CH$_2$Cl$_2$ | 25 |
| 4 | CH$_2$Cl$_2$, 3 washings | 1 |
| 5 | CHCl$_3$, 2 washings | 1 |
| 6 | Mixture containing 10% of TEA and 90% of CHCl$_3$, 2 washings | 2 |
| 7 | CHCl$_3$, 2 washings | 1 |
| 8 | Ethanol, 2 washings | 1 |
| 9 | CH$_2$Cl$_2$, 2 washings | 1 |
| 10 | 3 equivalents of Boc-aminoacid dissolved in a CH$_2$Cl$_2$—DMF mixture, 3 equivalents of DCC or DIC dissolved in CH$_2$Cl$_2$ | 60-varying |
| 11 | CH$_2$Cl$_2$, 2 washings | 1 |
| 12 | Ethanol, 2 washings | 1 |

A ninhydrin test is carried out after each step [E. Kaiser et al.: Anal. Biochem. 34, 595 (1970)]; the above cycle is repeated starting from Step 5 when a free amino group is detected. After carrying out the last step, the weight of the Glp-His(Tos)-Trp-Ser(oBzl)-Tyr(oBzl)-Aa-Leu-Arg(Tos)-Pro-Gly peptide resin shows that the yield of the aimed product is 344 mg (65% as ΔW). (The molecular weight of the protected peptide is 1764.92).

Step (b)

Cleavage by using hydrogen fluoride

The protective groups are removed and simultaneously the peptide is splitted off from the resin in a single step by using liquid anhydrous hydrogen fluoride [S. Sakakibara et al.: Bull. Soc. Japan 40, 2164 (1967)]. To the peptide resin obtained in the preceding Step (a), 5 ml of anisole and 100 mg of dithiothreitol are added. Then 20 ml of hydrogen fluoride are condensed to this mixture and the stirring is continued for one hour. After this period, the hydrogen fluoride is removed by a nitrogen stream, the residue is suspended in abs. ether and filtered. The solid residue is washed with 50% acetic acid and the filtrate is evaporated at a temperature of 37° C. The thus-obtained decapeptide.HF salt (371 mg) is directly subjected to gel chromatography.

Step (c)

Gel chromatography

The product obtained in the preceding Step (b) is purified on a Sephadex G-25 column (2.5×100 cm) by using 20% acetic acid as eluant. The separation is followed by UV absorption (measured at 280 nm) and TLC. The fractions containing the decapeptide are collected and lyophilized to give the purified product in a yield of 202 mg (54%).

Step (d)

Preparative HPLC

C$_{18}$-silica gel LRP-1 (13–24 μm, Whatman) type preparative HPLC column (2.5×45 cm) is used for this purpose. The equilibrium is established by using a mixture containing 15% of methanol and 85% of a 20% acetic acid solution. After reaching equilibrium, 202 mg of the product purified by gel chromatography are applied as dissolved in the above mixture. The elution is started with a linear gradient series from a mixture containing 15% of methanol and 85% of 20% acetic acid up to a mixture containing 25% of methanol and 75% of 20% acetic acid, continued with a mixture containing 40% of methanol and 60% of 20% acetic acid and finished with a mixture containing 80% of methanol and 20% of 20% acetic acid. These operations are carried out at a flow rate of 2 ml/min under a pressure of $3.5 \times 10^5$ Pa. The fractions are examined at 280 nm and their content is controlled by using TLC. The thus-obtained pure [Aa$^6$]-gonadoliberin final product amounts to 123 mg (61.0%) after lyophilization, m.p.: 185°–192° C.

$[\alpha]_D^{20} = -63.2°$ (c=1, 0.1N acetic acid).

$R_f^1 - 0.17$.

The aminoacid analysis gave the following values: Ser 0.92; Glu 1.03; Pro 1.1; Gly 0.97; Leu 1.00; Tyr 0.95; His 1.08; Trp 0.83; Aa 0.90; Arg 1.05.

EXAMPLES 5 AND 6

The following compounds are prepared by using the process described in Example 4:

| No. of Example | Name of the compound | $R_f^5$ | Yield |
|---|---|---|---|
| 5 | [Aa$^6$, Trp$^7$, Leu$^8$]-gonadoliberin | 0.57 | 35% |
| 6 | [Mab$^6$, Phe$^7$, Gln$^8$]-gonadoliberin | 0.63 | 43% |

The aminoacid analyses of the compounds of Examples 5 and 6 gave the values summarized in the following Table:

| No. of Example | Ser | Glu | Pro | Gly | Leu | Tyr | Phe | His | Trp | Aa/Mab |
|---|---|---|---|---|---|---|---|---|---|---|
| 5 | 0.91 | 1.02 | 0.97 | 1.00 | 0.98 | 1.03 | — | 0.93 | 1.82 | 0.96 |
| 6 | 0.93 | 2.02 | 1.12 | 1.00 | — | 0.97 | 1.07 | 0.95 | 0.87 | 0.89 |

EXAMPLE 7

Preparation of injection solutions for intramuscular, subcutaneous or intravenous administration (a) The gonadoliberin derivative of the general formula (I) is dissolved to a concentration of 1 to 10 mg/ml in distilled water, physiological saline or buffered aqueous solution. The solution is sterilized by filtration, then volumes containing 50 to 500 μg of the gonadoliberin derivative are filled into ampoules, lyophilized and finally the ampoules are sealed.

Before administration, the content of the ampoules is converted to a fresh solution by adding 1 to 10 ml of distilled water and a volume containing the desired dose is injected.

(b) A physiological saline solution or benzyl alcohol, respectively, containing the gonadoliberin derivative of the general formula (I) in a concentration of 20 to 500 μg/ml is filled into ampoules which are then sealed.

The thus-obtained solutions are suitable to direct administration.

What is claimed is:

1. Gonadoliberin nonapeptide ethylamide or decapeptide amide derivatives of the formula (I), $$\text{Glp-His-Trp-Ser-Tyr-}X_1\text{-}X_2\text{-}X_3\text{-Pro-}X_4 \quad (I)$$

wherein
$X_1$ stands for a 2-aminobenzoic or 3-aminobenzoic acid group;
$X_2$ stands for a leucyl, tryptophyl or phenylalanyl group;
$X_3$ means an arginyl, leucyl or glutaminyl group; and
$X_4$ represents a glycylamide or ethylamide group, as well as their acid addition salts.

2. A luteinizing and follicle-stimulating hormone releasing pharmaceutical composition, and a composition for reproduction biological purposes which comprises as the active ingredient a gonadoliberin derivative of the formula (I) as defined in claim 1, wherein $X_1$, $X_2$, $X_3$ and $X_4$ are as defined in claim 1, or a pharmaceutically acceptable acid addition salt thereof in admixture with carriers and/or additives commonly used in the pharmaceutical or veterinary medicine industry.

3. The derivative of formula I of claim 1, which is [Aa$^6$, Gln$^8$, desGly$^{10}$]-gonadoliberin ethylamide.

4. The derivative of formula I of claim 1, which is [Aa$^6$, desGly$^{10}$]-gonadoliberin ethylamide.

* * * * *